US010457616B2

(12) United States Patent
Suriye et al.

(10) Patent No.: US 10,457,616 B2
(45) Date of Patent: Oct. 29, 2019

(54) METATHESIS CATALYST AND PROCESS FOR PRODUCING OLEFIN

(71) Applicant: SMH Co., Ltd, Bangkok (TH)

(72) Inventors: Kongkiat Suriye, Samutprakan (TH); Burin Khemthong, Samutprakan (TH); Mathukorn Sanwanich, Bangkok (TH)

(73) Assignee: SMH Co., Ltd., Bangkok (TH)

(*) Notice: Subject to any disclaimer, the term of this patent is extended or adjusted under 35 U.S.C. 154(b) by 10 days.

(21) Appl. No.: 15/515,703

(22) PCT Filed: Jan. 29, 2016

(86) PCT No.: PCT/EP2016/051874
§ 371 (c)(1),
(2) Date: Mar. 30, 2017

(87) PCT Pub. No.: WO2016/120423
PCT Pub. Date: Aug. 4, 2016

(65) Prior Publication Data
US 2017/0305816 A1 Oct. 26, 2017

(30) Foreign Application Priority Data
Jan. 30, 2015 (EP) .................. 15153277

(51) Int. Cl.
B01J 23/02 (2006.01)
C07C 6/04 (2006.01)
B01J 37/04 (2006.01)
B01J 27/232 (2006.01)
B01J 27/25 (2006.01)
B01J 29/076 (2006.01)
B01J 29/16 (2006.01)
B01J 23/30 (2006.01)
B01J 37/02 (2006.01)
B01J 37/08 (2006.01)
B01J 38/12 (2006.01)
B01J 23/00 (2006.01)
B01J 23/24 (2006.01)
B01J 23/32 (2006.01)
B01J 29/48 (2006.01)
B01J 29/69 (2006.01)
B01J 29/78 (2006.01)

(52) U.S. Cl.
CPC ............... C07C 6/04 (2013.01); B01J 23/02 (2013.01); B01J 23/30 (2013.01); B01J 27/232 (2013.01); B01J 27/25 (2013.01); B01J 29/076 (2013.01); B01J 29/166 (2013.01); B01J 37/0201 (2013.01); B01J 37/04 (2013.01); B01J 37/08 (2013.01); B01J 23/007 (2013.01); B01J 23/24 (2013.01); B01J 23/32 (2013.01); B01J 29/163 (2013.01); B01J 29/48 (2013.01); B01J 29/69 (2013.01); B01J 29/7815 (2013.01); B01J 29/7876 (2013.01); B01J 38/12 (2013.01); C07C 2521/04 (2013.01); C07C 2521/08 (2013.01); C07C 2521/10 (2013.01); C07C 2523/30 (2013.01); C07C 2527/232 (2013.01); C07C 2529/08 (2013.01); C07C 2529/16 (2013.01); Y02P 20/52 (2015.11); Y02P 20/584 (2015.11)

(58) Field of Classification Search
CPC ........ B01J 23/30; B01J 37/0201; B01J 37/04; B01J 37/08; B01J 23/007; B01J 23/02; B01J 23/24; B01J 23/32; B01J 27/232; B01J 27/25; B01J 29/076; B01J 29/163; B01J 29/166; B01J 29/48; B01J 29/69; B01J 29/7815; B01J 29/7876; B01J 38/12; C07C 2521/08; C07C 2523/30; C07C 2527/232; C07C 2529/08; C07C 6/04; C07C 11/06; C07C 2521/04; C07C 2521/10; C07C 2529/16
See application file for complete search history.

(56) References Cited

U.S. PATENT DOCUMENTS

| 5,120,896 A | 6/1992 | Kemp et al. | |
|---|---|---|---|
| 2008/0312485 A1* | 12/2008 | Takai | C07C 1/24 585/640 |
| 2010/0145126 A1* | 6/2010 | Takai | C07C 6/04 585/646 |
| 2010/0191030 A1 | 7/2010 | Ikenaga | |
| 2011/0152595 A1 | 6/2011 | Takai et al. | |
| 2012/0095275 A1* | 4/2012 | Coleman | C07C 2/36 585/329 |
| 2013/0252804 A1 | 9/2013 | Ramachandran et al. | |

FOREIGN PATENT DOCUMENTS

| CN | 105102407 A | 11/2015 | |
|---|---|---|---|
| EP | 2786978 A1 * | 10/2014 | ............. B01J 21/10 |
| EP | 2786978 A1 | 10/2014 | |
| WO | 01/12570 A1 | 2/2001 | |
| WO | 2016/068814 A1 | 5/2016 | |
| WO | 2016/150794 A1 | 9/2016 | |

OTHER PUBLICATIONS

International Search Report and Written Opinion—PCT/EP2016/120423—dated Jun. 1, 2016.
H. Liu et al. (Journmal of Natural Gas Chemistry 18 (2009), p. 331-336).
Banks et al. (Journal of Molecular Catalysis 28 (1-3) (1985) p. 117-131).

* cited by examiner

Primary Examiner — Sharon Pregler
(74) Attorney, Agent, or Firm — Banner & Witcoff, Ltd.

(57) ABSTRACT

The present invention provides a catalyst comprising a transition metal, an inorganic support, a zeolite, and a layered double hydroxide. Using of the catalyst according to the present invention in an olefin production process exhibits high activity and high selectivity with decreased deactivation rate, therefore longer reaction cycle can be performed and catalyst life is prolonged.

20 Claims, No Drawings

METATHESIS CATALYST AND PROCESS FOR PRODUCING OLEFIN

CROSS-REFERENCE TO RELATED APPLICATIONS

This application is a U.S. National Stage application under 35 U.S.C. § 371 of International Application PCT/EP2016/051874 (published as WO 2016/120423 A1), filed Jan. 29, 2016, which claims the benefit of priority to EP 15153277.7, filed Jan. 30, 2015. Benefit of the filing date of each of these prior applications is hereby claimed. Each of these prior applications is hereby incorporated by reference in its entirety.

TECHNICAL FIELD

The present invention relates to catalyst and process for producing olefin by olefin metathesis reaction.

BACKGROUND

Metathesis is one of a crucial reaction for the petrochemical industry, especially the cross-metathesis of ethene and butene which is an economical mean to produce highly demanded propene.

In a typical industrial metathesis process, the metathesis catalyst deactivates over time and hence requires periodically regeneration. Regeneration process generally involves treatment of the deactivated catalyst with an oxidizing gas at a high temperature to burn off poisonous substances and heavy deposits formed during the reaction. There is limited number of time that a catalyst should be subjected to such regeneration process because severe condition employed can alter some specific properties of the catalyst such as surface area and therefore reduce its efficiency.

It was found that during a reaction of ethene and butene to produce propene, 1,3-butadiene is formed as a byproduct. 1,3-butadiene, even at a low concentration in the system, induces coke formation on the catalyst surface which results in deactivation of the catalyst. To reduce such effect of 1,3-butadiene to the deactivation rate, the metathesis process can be carried out in the presence of hydrogen, as disclosed in patent publications number U.S. 20100145126 A1, U.S. 20130252804 A1, and U.S. 20100191030 A1. However, the presence of hydrogen would result in hydrogenation of propene product and therefore reduce propene product yield.

SUMMARY

It is an object of the present invention to provide an improved catalyst overcoming drawbacks of the prior art. In particular, it is an object of the present invention to provide a catalyst featuring slower drop of product yield to avoid frequently regenerating the catalyst. It is a further object to provide a catalyst for olefin metathesis reaction allowing suppression of formation of unwanted by-products, such as 1,3-butadiene in the reaction of ethene and butene.

This object is achieved by a metathesis catalyst, comprising: a) a transition metal selected from Group VIA and VIIA of the Periodic Table of Elements; b) an inorganic support; c) 0.1-60 parts by weight of a zeolite; and d) 0.1-80 parts by weight of a layered double hydroxide.

The present invention also provides an improved olefin production process comprising contacting a feed stream comprising an olefin with the metathesis catalyst according to the present invention.

Using of the metathesis catalyst according to the present invention in an olefin production process exhibits high activity and high selectivity with decreased deactivation rate, therefore longer reaction cycle can be performed and catalyst life is prolonged.

DETAILED DESCRIPTION

A metathesis catalyst according to the present invention comprises a) a transition metal selected from Group VIA and VIIA of the Periodic Table of the Elements, b) an inorganic support, c) 0.1-60 parts by weight of a zeolite, and d) 0.1-80 parts by weight of a layered double hydroxide.

In preferred embodiments, parts by weight with respect to constituents of the inventive catalyst is percent by weight.

In context of the present invention, the term "Group VIA" is related to the group 6 elements of the chromium group, in particular Cr, Mo and W. In the same way, the term "Group VIIA" is related to the group 7 elements of the manganese group, in particular Mn, Te and Re.

It is preferable that the transition metal used in this catalyst is selected from molybdenum, tungsten, and rhenium, which are highly active in metathesis reaction. The transition metal can be present in various forms including a metal element, oxide, sulfide, hydride, and hydroxide of the transition metal. In particular, oxides such as $WO_3$, $MoO_3$, and $Re_2O_7$ are preferable, and $WO_3$ is even more preferable. In an embodiment, the catalyst of the present invention comprises 1 to 15 parts by weight of the transition metal, preferably 7 to 11 parts by weight.

The transition metal is supported on an inorganic support. A variety of inorganic supports is well known in the art. The types of the inorganic support are not particularly limited. In a preferred embodiment, the inorganic support is selected from silica, alumina, titania, zirconia, and mixtures thereof, preferably silica.

The metathesis catalyst comprises 0.1-60 parts by weight of a zeolite. The types of zeolite are not limited, but can be preferably selected from ZSM-5, X-zeolite, Y-zeolite, beta-zeolite, MCM-22, ferrierite, and mixtures thereof. In a preferred embodiment, the zeolite is selected from ZSM-5, Y-zeolite, and ferrierite, more preferably Y-zeolite.

Also in another preferred embodiment, the content of zeolite in the metathesis catalyst is in the range of 0.5-30 parts by weight, more preferably 1-20 parts by weight, relative to the total weight of the catalyst.

The layered double hydroxides (LDH), also known as anionic clays or hydrotalcite-like materials, are a family of materials having a unique structure containing positively charged layers with charge-balancing anions and water interlayers. The general chemical formula of the layered double hydroxides can be written as:

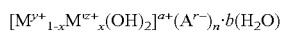

wherein
M is a first metal;
M' is a second metal;
A is an anion;
x is a number, preferably in the range of 0.1 to 0.9;
y is a charge number of the first metal, preferably equal to 1 or 2;
z is a charge number of the second metal, preferably equal to 3 or 4;
a is determined by x, y, and z, preferably a=(1−x)y+xz−2;
r is a charge number of the anion;
n is determined by a and r, preferably n=a/r;

b is a number of water molecules, preferably in the range of 0-10.

The first metal (M) and the second metal (M') can be alkali, alkaline earth, transition, or other metals. In a preferred embodiment, the first metal is selected from Li, Ca, Mg, Mn, Fe, Co, Ni, Cu, Zn, and mixtures thereof, preferably Ca and/or Mg. In another preferred embodiment, the second metal is selected from Al, Ga, In, Mn, Fe, Co, Cr, Ni, V, Ti, Zr, Y, and mixtures thereof, preferably Al.

Examples of the anions include chloride, bromide, carbonate, bicarbonate, hydrogen phosphate, dihydrogen phosphate, nitrite, borate, nitrate, sulphate, phosphate, hydroxide, fluoride, iodide, and mixtures thereof. In a very preferred embodiment, the anion is selected from carbonate and nitrate.

Effect of the layered double hydroxide on the catalyst conversion, selectivity, and byproduct formation can be observed even at a low concentration. In an embodiment, the metathesis catalyst comprises 0.5-50 parts by weight, more preferably 1-30 parts by weight of the layered double hydroxide relative to the total catalyst weight.

Components of the metathesis catalyst according to the present invention can be co-existed in various manners. For example, inorganic support, zeolite, and LDH could be mixed prior to transition metal deposition. For another example, transition metal could be deposited on LDH prior to mixing with zeolite and inorganic support.

The object of the present invention is further achieved by the inventive metathesis catalyst obtainable by a preparation process comprising a) mixing an inorganic support with a zeolite to obtain a mixture thereof; b) depositing a transition metal on the mixture of the inorganic support and the zeolite to obtain a deposited mixture; and c) mixing the deposited mixture with the layered double hydroxide to obtain the metathesis catalyst.

The mixture of the inorganic support and the zeolite can be easily obtained by physically mixing. The metal depositing technique may be conventional in the art without limitation. In a typical case, a compound of the transition metal is impregnated onto the mixture of the inorganic support and the zeolite.

In a specific embodiment, the metal deposited mixture is dried and/or calcined before mixing with the layered double hydroxide. Drying and calcining methods are not particularly limited. In a specifically preferred embodiment, the metal deposited mixture is calcined in air at 400° C. to 700° C. for 0.5 to 12 hours prior to mixing with the layered double hydroxide.

Shape and size of the metathesis catalyst is not limited and may be selected appropriately depending on process requirement. To facilitate formation of the catalyst, appropriate binder component, such as inorganic oxide, inorganic oxide sol, or clay, may be further added to the catalyst.

The object of the present invention is still further achieved by an olefin production process comprising contacting a feed stream comprising an olefin with the inventive metathesis catalyst.

The feed stream may include a linear or cyclic olefin having 2-12 carbon atoms. In a preferred embodiment, the feed stream comprises a linear olefin selected from the group consisting of C2 linear olefin, C3 linear olefin, C4 linear olefin, C5 linear olefin, C6 linear olefin, and mixtures thereof. In a more preferred embodiment, the feed stream comprises ethene and n-butene or ethene and n-pentene wherein propene being a preferred product. The feed stream preferably comprising less than 5 wt % of dienes and less than 5 wt % of acetylenes, more preferably less than 1 wt % of dienes and less than 1 wt % of acetylenes. Optionally, in some cases the feed stream may further comprise paraffins, preferably within the range of 0 to 50 wt %, wherein the paraffins does not react or convert when contacted with the metathesis catalyst in the olefin production process according to the present invention.

The operating conditions for the inventive process to be carried out include a temperature in the range of 100-600° C., preferably 200-450° C. and a pressure in the range of 0-50 bar gauge. The operational mode of the process of the invention can be appropriately selected from any known art including fixed bed, fluidized bed, swing bed, and moving bed, with fixed bed being generally preferable. The process can be efficiently carried out without the presence of any additional co-catalyst or a guard bed.

Prior to contacting with the olefin feedstock, the metathesis catalyst may be treated with an inert gas, oxidizing gas, or reducing gas at a heated environment, preferably in the range of 200-700° C.

The metathesis catalyst of the present invention can be regenerated; therefore, the olefin production process can further comprise a regeneration step. A typical metathesis catalyst regeneration procedure involves contacting a degraded catalyst with an oxidizing gas at a high temperature to burn off poisonous substances and heavy deposits formed on the catalyst during the reaction period. Other known regeneration techniques can be employed without limitation.

The metathesis catalyst and the olefin production process using the metathesis catalyst of the present invention are advantageous in that they provide a more stable metathesis reaction, which exhibits through an extended cycle time. This also results in a more economically attractive industrial process. Embodiments and advantageous effects of the present invention are further illustrated in the following examples without limiting the scope of the invention.

EXAMPLES

Example 1

Comparative

A metathesis catalyst comprising 9 wt % $WO_3$ on silica support was packed in a tube reactor. A feed stream comprising ethene and 2-butene was supplied to the reactor at the weight hourly space velocity (WHSV) of 1.4 $hr^{-1}$ and the catalyst bed was controlled to be at 350° C. and 22 bar gauge.

Effluent from the reactor was analyzed. At 5 hours on stream, n-butene conversion was 54% and propene selectivity was 92%. At 15 hours on stream, n-butene conversion was 27% and propene selectivity was 89%. Average 1,3-butadiene formation was 170 ppm and average C5+ formation was less than 5 wt % relative to the total effluent stream.

Example 2

Comparative

A metathesis catalyst was obtained by physically mixing 9 wt % $WO_3$ on silica support with Mg—Al—$CO_3$ layered double hydroxide in the ratio of 10:1 by weight. The catalyst was packed in a tube reactor. A feed stream comprising ethene and 2-butene was supplied to the reactor at the weight hourly space velocity (WHSV) of 1.4 $hr^{-1}$ and the catalyst bed was controlled to be at 350° C. and 22 bar gauge.

Effluent from the reactor was analyzed. At 5 hours on stream, n-butene conversion was 65% and propene selectivity was 94%. At 15 hours on stream, n-butene conversion was 47% and propene selectivity was 90%. Average 1,3-butadiene formation was 198 ppm and average C5+ formation was less than 5 wt % relative to the total effluent stream.

Example 3

A metathesis catalyst was obtained by physically mixing 9 wt % $WO_3$ on a support containing 95 wt % of silica and 5 wt % of Y-zeolite with Mg—Al—$CO_3$ layered double hydroxide in the ratio of 10:1 by weight. The catalyst was packed in a tube reactor. A feed stream comprising ethene and 2-butene was supplied to the reactor at the weight hourly space velocity (WHSV) of 1.4. $hr^{-1}$ and the catalyst bed was controlled to be at 350° C. and 22 bar gauge.

Effluent from the reactor was analyzed. At 5 hours on stream, n-butene conversion was 64% and propene selectivity was 95%. At 15 hours on stream, n-butene conversion was 68% and propene selectivity was 94%. Average 1,3-butadiene formation was 9 ppm and average C5+ formation was less than 5 wt % relative to the total effluent stream.

Example 4

A metathesis catalyst was obtained by physically mixing 9 wt % $WO_3$ on a support containing 95 wt % of silica and 5 wt % of Y-zeolite with Mg—Al—$CO_3$ layered double hydroxide in the ratio of 10:0.5 by weight. The catalyst was packed in a tube reactor. A feed stream comprising ethene and 2-butene was supplied to the reactor at the weight hourly space velocity (WHSV) of 1.4 $hr^{-1}$ and the catalyst bed was controlled to be at 350° C. and 22 bar gauge.

Effluent from the reactor was analyzed. At 5 hours on stream, n-butene conversion was 57% and propene selectivity was 80%. At 15 hours on stream, n-butene conversion was 35% and propene selectivity was 78%. Average 1,3-butadiene formation was 19 ppm and average C5+ formation was less than 5 wt % relative to the total effluent stream.

Example 5

A metathesis catalyst was obtained by physically mixing 9 wt % $WO_3$ on a support containing 95 wt % of silica and 5 wt % of Y-zeolite with Mg—Al—$CO_3$ layered double hydroxide in the ratio of 1:1 by weight. The catalyst was packed in a tube reactor. A feed stream comprising ethene and 2-butene was supplied to the reactor at the weight hourly space velocity (WHSV) of 1.4 $hr^{-1}$ and the catalyst bed was controlled to be at 350° C. and 22 bar gauge.

Effluent from the reactor was analyzed. At 5 hours on stream, n-butene conversion was 64% and propene selectivity was 87%. At 15 hours on stream, n-butene conversion was 60% and propene selectivity was 84%. Average 1,3-butadiene formation was 64 ppm and average C5+ formation was less than 5 wt % relative to the total effluent stream.

Example 6

A metathesis catalyst was obtained by physically mixing 9 wt % $WO_3$ on a support containing 95 wt % of silica and 5 wt % of Y-zeolite with Ca—Al—$CO_3$ layered double hydroxide in the ratio of 10:1 by weight. The catalyst was packed in a tube reactor. A feed stream comprising ethene and 2-butene was supplied to the reactor at the weight hourly space velocity (WHSV) of 1.4 $hr^{-1}$ and the catalyst bed was controlled to be at 350° C. and 22 bar gauge.

Effluent from the reactor was analyzed. At 5 hours on stream, n-butene conversion was 64% and propene selectivity was 95%. At 15 hours on stream, n-butene conversion was 65% and propene selectivity was 91%. Average 1,3-butadiene formation was 37 ppm and average C5+ formation was less than 5 wt % relative to the total effluent stream.

Example 7

Comparative

A metathesis catalyst was obtained by physically mixing 9 wt % $WO_3$ on a support containing 95 wt % of silica and 5 wt % of Y-zeolite with magnesium oxide in the ratio of 1:1 by weight. The catalyst was packed in a tube reactor. A feed stream comprising ethane and 2-butene was supplied to the reactor at the weight hourly space velocity (WHSV) of 1.4 $hr^{-1}$ and the catalyst bed was controlled to be at 350° C. and 22 bar gauge.

Effluent from the reactor was analyzed. At 5 hours on stream, n-butene conversion was 65% and propene selectivity was 91%. At 15 hours on stream, n-butene conversion was 60% and propene selectivity was 72%. Average 1,3-butadiene formation was 238 pm and average C5+ formation was less than 8 wt % relative to the total effluent stream.

Results from the above examples are summarized in the Table 1 below.

TABLE 1

| Example | Zeolite (wt %) | LDH species | LDH (wt %) | n-Butene conversion (wt %) | | Propene selectivity (wt %) | | Avg. 1,3-butadiene formation (ppm) | Avg. C5+ formation (ppm) |
|---|---|---|---|---|---|---|---|---|---|
| | | | | 5 h | 15 h | 5 h | 15 h | | |
| 1 | — | — | — | 54 | 27 | 92 | 89 | 170 | <5 |
| 2 | — | MgAlCO$_3$ | 9 | 65 | 47 | 94 | 90 | 198 | <5 |
| 3 | 4.1 | MgAlCO$_3$ | 9.1 | 64 | 68 | 95 | 94 | 9 | <5 |
| 4 | 4.3 | MgAlCO$_3$ | 4.8 | 57 | 35 | 80 | 78 | 19 | <5 |
| 5 | 2.3 | MgAlCO$_3$ | 50 | 64 | 60 | 87 | 84 | 64 | <5 |
| 6 | 4.1 | CaAlCO$_3$ | 9.1 | 64 | 65 | 95 | 91 | 37 | <5 |
| 7 | 2.3 | — | — | 65 | 160 | 91 | 72 | 238 | <8 |

It can be seen from the results of the above examples that incorporating zeolite and LDH into a metathesis catalyst results in lower 1,3-butadiene formation during metathesis reaction, and slower drop of product yield can be observed.

The features disclosed in the foregoing description and the accompanying claims may, both separately or in any combination, be material for realizing the invention in diverse forms thereof.

The invention claimed is:

1. A metathesis catalyst, comprising:
    a) a transition metal selected from the group consisting of chromium, molybdenum, tungsten, manganese, technetium, and rhenium;
    b) an inorganic support;
    c) 0.1-60 percent by weight of a zeolite; and
    d) 0.1-80 percent by weight of a layered double hydroxide.

2. The metathesis catalyst according to claim 1, wherein the transition metal is selected from the group consisting of molybdenum, tungsten, and rhenium.

3. The metathesis catalyst according to claim 1 comprising 1-15 percent by weight of the transition metal.

4. The metathesis catalyst according to claim 1, wherein the inorganic support is selected from the group consisting of silica, alumina, titania, zirconia, and mixtures thereof.

5. The metathesis catalyst according to claim 1 wherein the zeolite is selected from the group consisting of ZSM-5, X-zeolite, Y-zeolite, beta-zeolite, MCM-22, ferrierite, and mixtures thereof.

6. The metathesis catalyst according to claim 1 comprising 0.5-30 percent by weight of the zeolite.

7. The metathesis catalyst according to claim 1 wherein the layered double hydroxide comprises a first metal selected from the group consisting of Li, Ca, Mg, Mn, Fe, Co, Ni, Cu, Zn, and mixtures thereof.

8. The metathesis catalyst according to claim 7 wherein the layered double hydroxide comprises a second metal selected from the group consisting of Al, Ga, In, Mn, Fe, Co, Cr, Ni, V, Ti, Zr, Y, and mixtures thereof, wherein said second metal is different from said first metal.

9. The metathesis catalyst according to claim 1 wherein the layered double hydroxide comprises an anion selected from the group consisting of chloride, bromide, carbonate, bicarbonate, hydrogen phosphate, dihydrogen phosphate, nitrite, borate, nitrate, sulphate, phosphate, hydroxide, fluoride, iodide, and mixtures thereof.

10. The metathesis catalyst according to claim 1 wherein the metathesis catalyst is obtainable by a preparation process comprising:
    a) mixing the inorganic support with the zeolite to obtain a mixture thereof;
    b) depositing the transition metal on the mixture of the inorganic support and the zeolite to obtain a deposited mixture; and
    c) mixing the deposited mixture with the layered double hydroxide to obtain the metathesis catalyst.

11. The metathesis catalyst according to claim 10 wherein the preparation process further comprises drying and/or calcining the deposited mixture prior to mixing with the layered double hydroxide in step c).

12. An olefin production process comprising contacting a feed stream comprising an olefin with the metathesis catalyst according to claim 1.

13. The olefin production process according to claim 12 wherein the feed stream comprises ethylene, propylene, or a linear olefin selected from the group consisting of a C4 linear olefin, a C5 linear olefin, a C6 linear olefin, and mixtures thereof.

14. The metathesis catalyst of claim 4, wherein the inorganic support is silica.

15. The metathesis catalyst of claim 5 wherein the zeolite is selected from the group consisting of ZSM-5, Y-zeolite, ferrierite, and mixtures thereof.

16. The metathesis catalyst of claim 6 comprising 1-20 percent by weight of the zeolite.

17. The metathesis catalyst of claim 7 wherein the first metal is selected from the group consisting of Ca, Mg, and mixtures thereof.

18. The metathesis catalyst of claim 8 wherein the second metal is Al.

19. The metathesis catalyst of claim 1, comprising 1-30 percent by weight of the layered double hydroxide.

20. The olefin production process of claim 13, wherein the feed stream comprises (i) ethylene and n-butene or (ii) ethylene and n-pentene, and wherein the process further comprises withdrawing an effluent stream obtained following the contacting of the feed stream with the metathesis catalyst, said effluent stream comprising propylene formed by a reaction of said (i) ethylene and n-butene or (ii) ethylene and n-pentene, by olefin metathesis.

* * * * *